United States Patent [19]

Fogel

[11] Patent Number: 5,620,682
[45] Date of Patent: Apr. 15, 1997

[54] SUNSCREEN COMPOSITIONS

[75] Inventor: Arnold W. Fogel, Upper Saddle River, N.J.

[73] Assignee: Bernel Chemical Co., Englewood Cliffs, N.J.

[21] Appl. No.: 37,338

[22] Filed: Mar. 25, 1993

[51] Int. Cl.$^6$ .................... A61K 7/42; A61K 7/44
[52] U.S. Cl. ................ 424/60; 424/59; 514/937; 514/938
[58] Field of Search ............ 424/59, 60; 514/937, 514/938

[56] References Cited

U.S. PATENT DOCUMENTS

| | | | |
|---|---|---|---|
| 4,559,226 | 12/1985 | Fogel et al. | 424/66 |
| 4,929,439 | 5/1990 | Cotteret et al. | 424/59 |
| 5,116,604 | 5/1992 | Fogel et al. | 424/59 |

OTHER PUBLICATIONS

AMA Lab, Inc. Evaluation Of SPF F–6–39–1 Mar. 1993.
AMA Lab, Inc. Evaluation Of SPF F–7–1–1 Mar. 1993.
AMA Lab, Inc. Evaluation OF SPF F–7–1–3 Mar. 1993.
AMA Lab, Inc. Evaluation Of SPF F–7–2–2 Mar. 1993.
AMA Lab, Inc. Evaluation Of SPF F–7–3–1 Mar. 1993.
Amphisol Updated, 1989 Bernel Chemical Co., Inc.
Amphisol Suntan Emulsions Bernel Chemical Co., Inc.
CUPL®PIC Bernel Chemical Co., Inc.
Elefac I–205 Bernel Chemical Co.
Formulating SPF 2–15 with Parsol MCX Bernel Chem Co., Inc.
New Emulsion Technology Bernel Chemical Co., Inc.
Three Surtan Oils Bernel Chemical Co., Inc.
Waterproof Suntan Lotion Bernel Chemical Co., Inc.

*Primary Examiner*—Shelley A. Dodson
*Attorney, Agent, or Firm*—Anthony D. Cipollone

[57] ABSTRACT

Novel Sunscreen compositions are demonstrated which are either water dispersible or waterproof without the inclusion of PABA, PABA derivatives, oxybenzone (Benzophenone 3), and any auxilliary UV-B or UV-A screen be they water or oil soluble. This is done by the use of p-methoxy-2-ethyl-hexyl cinnamate (Parsol MCX) and 1-(4-methoxylphenyl)-3-(4 tert-butyl-phenyl) propan 1–3 dione (Parsol 1789) as the only absorbers present.

The only common element in all the sunscreen composition demonstrated is the presence of the neopentanoate ester having the strutural formula

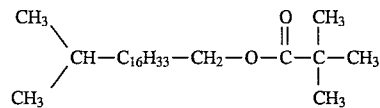

which is used for emolliency; moisturization and increasing the SPF factors. The unusually high SPF factors are a result of these unique compositions.

8 Claims, No Drawings

SUNSCREEN COMPOSITIONS

BACKGROUND OF THE INVENTION

The Novel Sunscreen Compositions presented in the instant invention had their genesis with the Petitioner's entry into this area of expertise and his continuous work in development and improvements in the field of Sunscreen emulsions, emollients and final formulations since April, 1982.

Initially, in 1982 the sunscreen molecule of choice was a derivative of p-amino benzoic acid, octyldimethyl p-amino benzoate.

Petitioner's work with formulations with p-methoxy-2-ethylhexyl cinnamate gave results equal or better than the use of octyl dimethyl p-amino benzoate.

The development continued with the new uses of diethanolamine cetylphospate and more recently, the use of potassium cetyl phosphate in sunscreen formulations to give oil in water emulsions which gave waterproof sunscreen formulations.

The Petitioner's further goal was to discover a water dispersible, self emulsifying surfactant that would be oil soluble and simultaneously have emollient properties with a desirable skin feel. This surfactant when added to $H_2O$ at room temperature would form its own oil in $H_2O$ emulsion and at the same time appear and feel like a cosmetic skin lotion. In addition, the surfactant would be stable, safe and effective at use concentrations.

The result of this effort is U.S. Pat. No. 4,559,226 which introduced at least two self-emulsifying alkoxylated esters having the structural formulas:

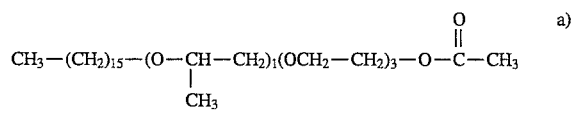

Trade name: Hetester ® PCA;

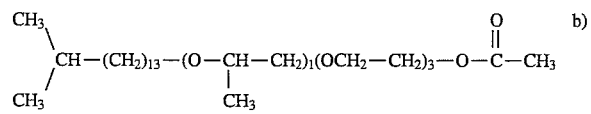

Trade name: Hetester ® PHA.

Increasing the hydrophilic portion of structure b, to cause water solubility, the resulting compound has the following structure:

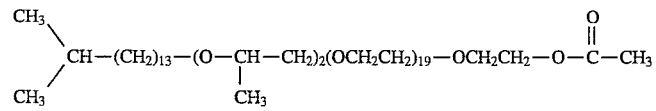

Trade name: CUPL ® PIC for which Patent Applications have been submitted.

The resulting compound, that is, CUPL® PIC became a fragrance solubilizer and oil in water emulsifier.

The aforementioned Hetesters® and CUPL® PIC proved to be excellent oil in water emulsifiers, emulsifying at least twice their own weight in oil. They further proved to be excellent pigment wetters and dispersers.

Both the Hetester® & CUPL® are synthesized and do not contain any animal derived components. They are free of phenolic and oleic groupings. These properties result in non-distortion of fragrances, less tachiness and excellent safety scores.

Recently, U.S. Pat. No. 5,116,604 was issued. The preferred embodiment of this invention has the following structure:

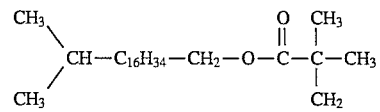

Trade name: Elefac ®.

This unique ester was produced by using a specific C-20 alcohol clearly defined in the Patent. The use of this specific C-20 alcohol resulted in a neopentanoate ester with an extraordinary emolliency that significantly enhances the sun protective factor (SPF) of a sunscreen formulation. In addition, it has these desirable properties: clear, low-freezing liquid, good color, odor, non-comedogenic, stable and safe. It is also a moisturizer and pigment wetter for cosmetic products.

Progressing further, various uses of the Hetester® and CUPL® surfactants in combination with the oil soluble ester, Elefac® I-205, gave a water thin, oil in water emulsion without the need for stabilizing water dispersible thickeners. The emulsion thus formed was stable for 3 months at 50° C. and had a perfect freeze/thaw stability.

The instant presentation is the end result of continuous pursuit of excellence in this field.

P-methoxy 2-ethyl-hexyl cinnamate produced results which were equal or better than the leading UV absorber in 1982, octyl dimethyl p-amino benzoate.

Diethanolamine cetyl phosphate is an unusual surfactant soluble in hot (85° C.) oil and water forming an oil in water emulsion which gives waterproof properties to the sunscreen formulation. Potassium cety phosphate, recently in use, gives similar results in the preferred embodiment.

The alkoxylated ester, Hetester® PHA, as above gives emulsions at room temperature.

The aforementioned alkoxylated ester CUPL® PIC is a solubilizer and emulsifier.

The neopentanoate ester, Elefac® I-205, is an SPF booster and emollient. The SPF boosting power of Elefac® is similar to the boosting power of water soluble UV-B additives.

Recently, Petitioner filed a Patent application for Novel Oil in Water Emulsions. The application introduced the use of Hetester PHA, CUPL® and Elefac® I-205 in combination to give water thin oil in water emulsion without the use of water dispersible gums. Using this emulsion system also resulted in unexpected high SPF readings with the use of p-methoxy-2-ethyl-hexyl cinnamate in the formulation.

Finally, using this emulsion system resulted in a water dispersible sunscreen formulation free of undesirable PABA, PABA derivatives and Benzophenone-3.

The use of this emulsion system and p-methoxy 2-ethyl-hexyl cinnamate and 1-(4-methoxyphenyl)-3-(4 tert-butyl-phenyl) propan-1,3-dione in the formulation also resulted in higher than expected SPF readings.

As a result of the Petitioner's work in this area, the present state of the art now includes sunscreen formulations exhibiting high SPF scores without the use of the undesirable PABA, PABA derivatives and Benzophenone-3 and other absorbers. In addition, some of the sunscreen formulations exhibit waterproof properties without the use of any polymers again with higher than expected SPF scores.

Sunscreen formulations have attained a major prominence as a result of recent studies indicating a relationship between skin cancer and exposure to the sun.

Sunscreen formulations for use on human skin are widely used and are available for diverse consumer needs. Different formulations give different Sun Protection Factors (SPF) values from 2–4 (minimal protection), 4–6 (moderate protection), 8–15 (maximum protection) and above 15 to indicate ultra sun protection.

There are a varied number of problems encountered in sunscreen compositions and the sunscreens used.

PABA and PABA derivatives used cause stains and may be problematic for people allergic to these chemicals. Benzphenone 3 presents solubilization problems in sunscreen formulations affecting stability of the finished formula and may also be sensitizing and cause alergy problems.

The polymers used in vehicles carrying waterproof sunscreens, also may cause non-consistent distribution on the skin and uneven sun protection making them undesirable by the consumer.

The introduction of the emulsifiers, Hetester® PHA, CUPL® PIC and Elefac® I-205 alone or in combination has eliminated all of the aformentioned problems encountered in sunscreen formulations.

OBJECTS, SUMMARY AND DESCRIPTION OF THE INVENTION

1. Object of the Invention

It is the object of this invention to introduce sunscreen compositions using only 1 UV-B and 1 UV-A sunscreen which would be PABA, PABA derivative, Benzophenone-3 and watersoluble sunscreen free in three different systems. These systems are:

a) moisturizer lotion which is water dispersible;

b) moisturizer lotion which is waterproof; and, c) waterproof oil.

These compositions are characterized by their stability. All compositions have a common element% the use of Elefac® I-205 in each formulation as the part of the vehicle carrying the sunscreen agents.

2. Summary and Description of the Invention

We have invented five sunscreen compositions which are herein demonstrated. All are PABA, PABA derivatives and Benzophenone-3 free. The common ingredient to all five sunscreen compositions introduced is the neopentoate ester, Elefac® I-205, U.S. Pat. No. 5,116,604 used for emolliency, moisturization and as an SPF booster.

Included in the sunscreen compositions introduced are three water dispersible sunscreen compositions and two waterproof sunscreen compositions sans polymer.

Following are the preferred embodiments of the invention:

The first composition is a water thin oil in water lotion made at 38 C which is UV absorber free and has an SPF score of 4.35. The vehicle itself is responsible for the SPF value. This composition is water dispersible. (F-6-39-1).

Composition Two is a viscous flowing oil in water lotion made at 38 C, scores an SPF of 13.08 while using only 7.5% of p-methoxy 2-ethyl-hexyl cinnamate, Parsol MCX, as the sole UVabsorber. This composition is a thickened version of the first composition with a UV-B absorber added. This composition also water dispersible. (F-7-1-1).

Composition three is a viscous flowing oil in water lotion made at 38 C. It is Composition Two with 1(4-Methoxyphenyl)-3-(4-tert-butyl-phenyl) propan-1,3 dione, Parsol 1789, added at 2.0% as the primary UV-A absorber. The SPF score was 17.3 This composition is also water dispersible. (F 7-1-3).

The Fourth Composition contains a different vehicle from the first three compositions which are based on a Hetester® PHA®, CUPD® PIC system. The vehicle in this composition is based on isostearic acid, cetyl alcohol and diethanolamine cetyl phosphate, Amphisol, as the emulsion system. Elefac® I-205 is the emollient. This composition is a flowing, oil in water lotion made at 85 C and scores an SPF of 17. It is a waterproof composition without the use of a waterproofing polymer. Only one UV-B (7.5%) sunscreen and one UV-A (2.0%) sunscreen are used. (F 7-2-2).

Composition Five is a water thin oil and a waterproof composition without the use of a waterproofing polymer. The only absorbers used are Parsol® MCX at 7.5% and Parsol® 1789 at 2.0%. It scores an SPF of 16. This waterproof oil has a perfect freeze thaw cycle. The emollients used are a combination of Elefac® I-205 and P P G-1 myristylacetate, Heteste PMA. (F-7-3-1).

What is claimed is:

1. A sunscreen compositon comprising an oil in water emulsion system wherein said emulsion system has an oil phase content from 20.0% to 40.0% by weight of said sunscreen composition wherein the said oil phase of the said emulsion system comprises a) an alkoxylated ester having the structural formula:

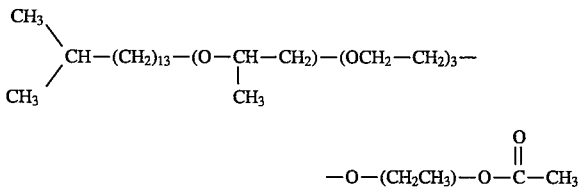

b) a second alkoxylated ester having the structural formula:

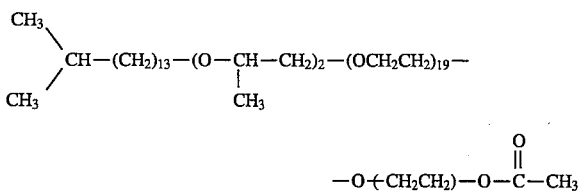

c) a neopentanoate ester having the structural formula:

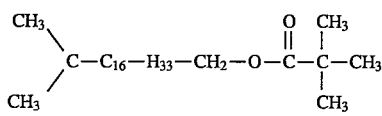

0.5% by weight methylchloroisothiazolinone (and) methylisothiazolinone of said sunscreen composition and a dionized water phase from 59.5% to 79.5% by weight of said sunscreen composition.

2. The said sunscreen compositon in claim 1 wherein said alkoxylated ester of said emulsion system having a structural formula (a) comprises 7.5% by weight of said sunscreen composition, said second alkoxylated ester having a structural formula (b) comprises 5.0% by weight of said sunscreen composition and the said neopentanoate ester having the structural formula (c) comprises 10.0% by weight of the said sunscreen composition and the said de-ionizes water phase comprises 77.45% of the said sunscreen composition.

3. A sunscreen composition comprising an oil in water emulsion system wherein said emulsion system has an oil phase content from 20.0% to 40.0% by weight of said sunscreen composition where in the oil phase of said emulsion system comprises:

(a) an alkoxylated ester having the structural formula:

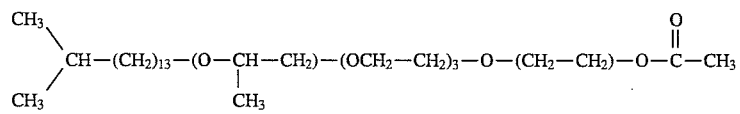

(b) a second alkoxylated ester having the structural formula:

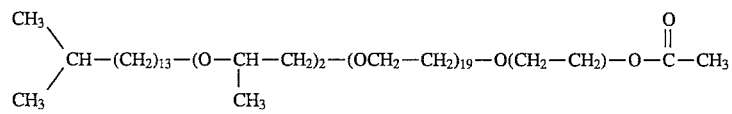

(c) a neopentanoate ester having the structural formula:

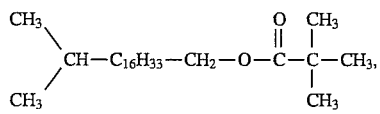

a dionized water phase from 49.7% to 69.7% by weight of said sunscreen compositions, 0.25% carbomer 940, 0.25% magnesium aluminum silicate, 0.25% triethanolamine, 99%, 0.5% methyl chloroisothiazolinone and methylisothiazolinone, 7.5% octylmethoxy cinnamate and 2.0% butyl methoxydibenzoylmethane.

4. The said sunscreen composition in claim 3 wherein the said alkoxylated ester having a structural formula (a) comprises 7.5% by weight of said sunscreen composition, a second alkoxylated ester having a structural formula (b) comprises 5.0% weight of said sunscreen composition and the said neopentanoate ester having said structural formula (c) comprises 10.0% by weight of said sunscreen composition.

5. A sunscreen composition comprising an oil in water emulsion system wherein said emulsion system has an oil phase content from 7.5% to 25.0% by weight of said sunscreen composition wherein the oil phase of said emulsion system is a neopentanoate ester having the structural formula:

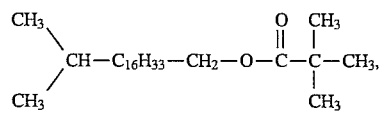

a deionized water phase from 52.7% to 70.2% by weight of said sunscreen composition, 4.0% glycerine, 0.75 magnesium silicate, 0.25% xanthan gum 4.0% isostearic acid, 1.0% cetyl alcohol, 2.0% diethanolamine cetyl phosphate, 0.5% simethicone, 2.0% methyl paraben, 2.0% propyl paraben and 7,5% octylmethoxy cinnanate and 2.0% butyl methoxy dibenzoylmethane.

6. The said sunscreen composition in claim 5 wherein the said neopentanoate having the structural formula,

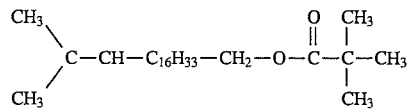

comprises 10.0% by weight of the said sunscreen formulation.

7. A waterproof sunscreen oil composition comprising by weight:

a) 4.0% isostearic acid b) 1.0% isocetyl alcohol c) an emulsion system comprising 1. 15.0% of a neopentanoate ester having the structural formula:

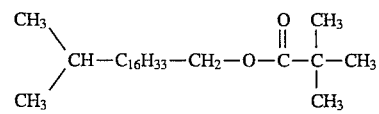

2. 15.0% propylene glycol myristyl ester acetate d) 25,0% cyclomethicone e) Two sunscreen agents:

1. 7.5% octyl methoxy cinnamate 2. 2.0% butyl methoxydibenzoylmethane f) 30.5% anhydrous SD 40 ethanol.

8. The said sunscreen composition in claim 7 comprising by % weight of said sunscreen composition a) said iosetearic acid, 4.0% b) said isocetyl alcohol, 1.0% c)
  1) said neopentanoate ester, 15.0%
  2) said propylene glycol myristyl ester acetate is 15.0% d) said cyclomethicone is 25.0% e)
  1) said octymethoxy cinnamate is 7.5%
  2) said butyl methoxydibenzoylmethane is 2.0% f) said anhydrous SD 40 ethanol is 30.50%.

* * * * *